(12) United States Patent
Zheng et al.

(10) Patent No.: US 10,459,052 B2
(45) Date of Patent: Oct. 29, 2019

(54) MAGNETIC RESONANCE CHEMICAL-SHIFT-ENCODED IMAGING METHOD, APPARATUS AND DEVICE

(71) Applicant: Shenzhen Institutes of Advanced Technology Chinese Academy of Sciences, Nanshan District, Shenzhen (CN)

(72) Inventors: Hairong Zheng, Guangdong (CN); Xin Liu, Guangdong (CN); Chuanli Cheng, Guangdong (CN); Chao Zou, Guangdong (CN)

(73) Assignee: SHENZHEN INSTITUTES OF ADVANCED TECHNOLOGY CHINESE ACADEMY OF SCIENCES, Nanshan District Shenzhen, Guangdong (CN)

( * ) Notice: Subject to any disclaimer, the term of this patent is extended or adjusted under 35 U.S.C. 154(b) by 0 days.

(21) Appl. No.: 16/067,204

(22) PCT Filed: Dec. 30, 2015

(86) PCT No.: PCT/CN2015/099923
§ 371 (c)(1),
(2) Date: Jun. 29, 2018

(87) PCT Pub. No.: WO2017/113208
PCT Pub. Date: Jul. 6, 2017

(65) Prior Publication Data
US 2019/0011515 A1 Jan. 10, 2019

(51) Int. Cl.
*G01R 33/56* (2006.01)
*G01R 33/48* (2006.01)
(Continued)

(52) U.S. Cl.
CPC .......... *G01R 33/4828* (2013.01); *A61B 5/055* (2013.01); *G01R 33/443* (2013.01);
(Continued)

(58) Field of Classification Search
CPC ............ G01R 33/4828; G01R 33/5602; G01R 33/565; G01R 33/5607; G01R 33/443;
(Continued)

(56) References Cited

U.S. PATENT DOCUMENTS 6,192,263 B1 * 2/2001 Ma .................... G01R 33/54
324/309
2005/0165296 A1 7/2005 Ma
(Continued)

FOREIGN PATENT DOCUMENTS

| CN | 1385711 | 12/2002 |
|----|---------|---------|
| CN | 102369454 | 3/2012 |

(Continued)

*Primary Examiner* — Alesa Allgood
(74) *Attorney, Agent, or Firm* — Woodard, Emhardt, Henry, Reeves & Wagner, LLP (57) ABSTRACT

Provided are a magnetic resonance chemical-shift-encoded imaging method, apparatus, and device, belonging to the technical field of magnetic resonance imaging. The method comprises: in a phasor-error plot established on the basis of a two-point magnetic resonance signal model, determining to be an initial seed point a pixel having a unique phasor and causing said plot to reach a minimal local value; according to the initial seed point, estimating the phasor value of a to-be-estimated pixel to obtain a field map; mapping and merging the field map at the highest resolution to obtain a reconstructed field map; determining a reconstructed seed point from the reconstructed field map, and estimating the reconstructed seed point to obtain the phasor value of the reconstructed to-be-estimated pixel; according to the reconstructed seed point and the phasor value of the reconstructed to-be-estimated pixel, obtaining two separate images having (Continued)

predetermined components. In the method, a region simultaneously containing two components is identified as a seed point, eliminating the deviation caused by phasor-value jump at high resolution and ensuring the correctness of the seed point ultimately selected.

20 Claims, 5 Drawing Sheets (51) Int. Cl.
    *A61B 5/055*    (2006.01)
    *G01R 33/44*    (2006.01)
    *G01R 33/46*    (2006.01)
    *G01R 33/485*    (2006.01)
    *G01R 33/565*    (2006.01)

(52) U.S. Cl.
    CPC ....... *G01R 33/4625* (2013.01); *G01R 33/485* (2013.01); *G01R 33/56* (2013.01); *G01R 33/5608* (2013.01); *G01R 33/56527* (2013.01)

(58) Field of Classification Search
    CPC .... G01R 33/243; G01R 33/462; A61B 5/055; A61B 6/00; G06T 7/0012
    See application file for complete search history.

(56) References Cited

U.S. PATENT DOCUMENTS

2015/0161784 A1* 6/2015 Ma ....................... G06K 9/6215
    382/131
2017/0011536 A1* 1/2017 Ma ....................... G06K 9/6215

FOREIGN PATENT DOCUMENTS

| CN | 103140167 | 6/2013 |
| CN | 103608693 | 3/2014 |
| WO | WO 2006/121827 | 11/2006 |
| WO | WO 2013/130587 | 9/2013 |

* cited by examiner

MAGNETIC RESONANCE CHEMICAL-SHIFT-ENCODED IMAGING METHOD, APPARATUS AND DEVICE

TECHNICAL FIELD

The present disclosure relates to a magnetic resonance chemical-shift-encoded imaging method, apparatus and device which belong to the technical field of magnetic resonance imaging.

BACKGROUND

The magnetic resonance chemical-shift-encoded imaging is an imaging method based on a chemical shift difference between components in a tissue, and can be obtained by acquiring signals at different echo times and fitting a mixed signal model. Clinically, the most common chemical-shift-encoded imaging is water-fat separation imaging which is mainly used in fat suppression, fat quantification and other applications. In a separation process, a $B_o$ local field may be corrected through multi-echo chemical-shift-encoded imaging, and meanwhile, images of pure water and pure fat may be obtained. However, in the event that the $B_o$ field bias is larger or an imaging tissue space is separated, traditional multi-echo chemical-shift-encoded imaging easily converges to a wrong local minimum value when $B_o$ field bias is estimated, thereby causing a result of reverse water-fat separation.

A principle of the multi-echo chemical-shift-encoded imaging is to assume that the tissue signal is obtained by simultaneously exciting different components, the chemical shifts of the components relative to water are known, and mathematical models between the signal and the components and between a $B_o$ field pattern and an echo time (TE) are fitted. In actual application of the chemical-shift-encoded imaging, the water-fat separation imaging is mostly used, that is, two components (i.e., water and fat) are separated through a multi-echo signal.

The common multi-echo water-fat separation imaging may be classified into a two-point separation technology and a multi-point (greater than 2) separation technology, depending on different numbers of the TEs of the multi-echo water-fat separation imaging. Generally, the two-point separation technology can only separate components having two chemical shifts, but in some applications requiring rapid imaging, the two-point separation technology has higher acquisition and imaging speed.

There is a two-point water-fat separation technology in a prior art. Such technology assumes that field patterns are distributed uniformly; two specific echo times are selected to respectively acquire in-phase (IP) and opposed-phase (OP) images of water and fat protons, and a water diagram and a fat diagram are obtained through simple addition and/or subtraction operation. To solve an affection caused by the non-uniform $B_o$ field, there is also a local growth-based two-point water-fat separation technology in the prior art. In such technology, a local growth path is determined using an angle difference between a to-be-estimated pixel point and a seed point, and a field pattern of the to-be-estimated pixel point is determined according to a difference between a candidate field pattern value of the to-be-estimated pixel point and a sum of field pattern values of all seed points within a neighborhood scope. However, such method may only obtain the separated images of the pure water and pure fat, and the pure water diagram and the pure fat diagram in the separated images have to be identified by adding additional information.

In addition, there is yet another two-point water-fat separation technology in the prior art. Such technology does not restrict the water and fat phases to be opposed in a second acquired image, but acquire a partially-opposed-phase (POP) image of water and fat. Two amplitude images of the water and the fat are obtained by virtue of a cosine law, and based on this, the candidate values of the two field patterns can be obtained; and then, an original image is segmented into a plurality of non-overlapped subblocks. A field pattern set having maximum field pattern similarity in each subblock is selected as an initial field pattern according to smooth characteristics of field pattern distribution in the subblock. The field pattern in the entire original image space is estimated from a candidate solution of the field pattern by using an extraction algorithm of a regional iteration field pattern. Finally, the separated water and fat images are obtained using a least square method. However, such method has a defect that a selection contradiction is easily to be presented in a field pattern extraction process, that is, different selection results are obtained when the field pattern is selected in different directions, causing the jump in the final field pattern.

SUMMARY

To solve the problem that the existing chemical-shift-encoded imaging method can only separate signals for two components but not separately identify one component and jump is present in a field pattern, the present disclosure proposes a magnetic resonance chemical-shift-encoded imaging method, apparatus and device, and specifically includes the following technical solution:

A magnetic resonance chemical-shift-encoded imaging method includes:

establishing a phasor-error spectrum based on a two-point magnetic resonance signal model in a sampled image at a predetermined resolution;

determining, a pixel point having a unique phasor value in the phasor-error spectrum and enabling the phasor-error spectrum to reach a local minimum value, as an initial seed point;

estimating a phasor value of a to-be-estimated pixel point according to the initial seed point to obtain a field pattern at the predetermined resolution;

mapping, at a highest resolution, the field patterns at the predetermined resolutions respectively to obtain a plurality of field patterns at the highest resolution, and merging the plurality of field patterns to obtain a reconstructed field pattern;

determining a reconstructed seed point from the reconstructed field pattern, and estimating based on the reconstructed seed point to obtain a phasor value of the reconstructed to-be-estimated pixel point; and obtaining separated images of two predetermined components according to the phasor values of the reconstructed to-be-estimated pixel point and the reconstructed seed point.

A magnetic resonance chemical-shift-encoded imaging apparatus includes:

a phase error spectrum establishing module configured to establish a phasor-error spectrum based on a two-point magnetic resonance signal model in a sampled image at a predetermined resolution;

a seed point selecting module configured to determine, a pixel point having a unique phasor value in the phasor-error spectrum and enabling the phasor-error spectrum to reach a local minimum value, as an initial seed point;

an estimation module configured to estimate a phasor value of a to-be-estimated pixel point according to the initial seed point to obtain a field pattern at the predetermined resolution;

a field pattern reconstructing module configured to map, at a highest resolution, the field patterns at the predetermined resolutions respectively to obtain a plurality of field patterns at the highest resolution, and merge the plurality of field patterns to obtain a reconstructed field pattern;

a phasor determining module configured to determine a reconstructed seed point in the reconstructed field pattern, and estimate based on the reconstructed seed point to obtain a phasor value of the reconstructed to-be-estimated pixel point; and an imaging module configured to obtain separated images of two predetermined components according to the phasor values of the reconstructed to-be-estimated pixel point and the reconstructed seed point.

The present disclosure has beneficial effects in that: a region including the two components may be identified as the seed point at a low resolution by estimating the field pattern at the low resolution, thereby increasing the quantity and distribution range of the seed points; and the plurality of field patterns at the high resolution are merged with a self-checking mechanism, thereby eliminating a deviation caused by the jump of the phasor value at the highest resolution, guaranteeing the correctness of final selection of the seed point and accurately identifying the signals of the two components.

DETAILED DESCRIPTION

In a prior art, a researcher proposes a two-point separation technology on the basis of the existing two-point separation method. Such technology does not restrict the in-phase of water and fat in a first acquired image, but restricts that a difference or sum between the water-fat phase difference $\theta_1$ in the first acquired image and the water-fat phase difference $\theta_2$ in a second acquired image is not be equal to 2n or integer multiples. In addition, there is another two-point separation technology which does not restrict the TE. Such technology converts the field pattern estimation into global energy minimization on a basis of obtaining candidate solutions of two groups of field patterns, and estimates the field patterns using a tree message propagation algorithm.

However, the above existing algorithm has disadvantages in that: in the above first two-point separation technology, the field pattern sets at the different subblocks are obtained, and then are directly spliced as initial field patterns for conducting regional iteration field pattern extraction. However, it will bring the defect that the selection contradiction is easily to be presented in the field pattern extraction process, that is, different selection results are obtained when the field pattern is selected in the different directions, causing the jump in the final field pattern. In the above second two-point separation technology, when an IP/IP image is processed, due to a phase difference n of the candidate solutions of the two groups of field patterns, the correct field pattern and the reversed field pattern have the same energy, causing that the tree message propagation algorithm easily falls into the reversal of the global field pattern.

With regard to the above disadvantages, the present disclosure proposes a two-point water-fat separation method. The method is an estimation method for a safest path-local growth strategy based on multiple resolutions and a self-checking field pattern, and can achieve the correct field pattern estimation and water-fat separation.

Figure 1:
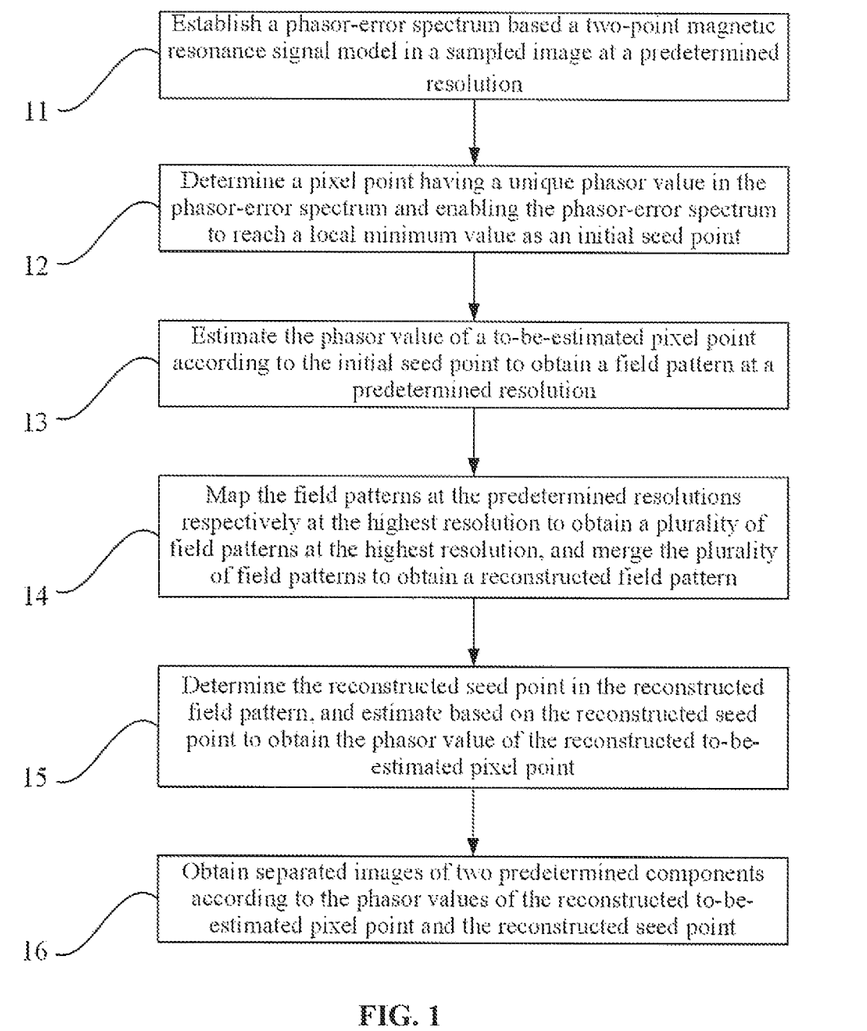
FIG. 1 is a flow chart illustrating a magnetic resonance chemical-shift-encoded imaging method in an example manner.

In combination with FIG. 1, the magnetic resonance chemical-shift-encoded imaging method proposed by the present disclosure includes:

Step 11, a phasor-error spectrum is established based on a two-point magnetic resonance signal model in a sampled image at a predetermined resolution.

In this step, a two-dimensional original image at the highest resolution is subjected to low-pass filtering and is undersampled according to a predefined undersampling coefficient, to obtain two-dimensional original images at different low resolutions; one pixel of the two-dimensional original images at the low resolutions corresponds to a plurality of pixels in the corresponding images at the highest resolutions; and the pixels are taken as a whole to depict the phasor-error (phasor-fitting error) spectrum thereof, i.e., a phasor-error spectrum of the one pixel at the low resolution.

Step 12, a pixel point having a unique phasor value in the phasor-error spectrum to enable the phasor-error spectrum to reach a local minimum value is determined as an initial seed point.

In this step, the phasor value that enables each pixel point to reach the local minimum value is determined according to the phasor-error spectrum. If the pixel point has a signal-to-noise ratio greater than a predetermined value and has a unique phasor value, the pixel point can be determined as a seed point.

Optionally, a process of determining the pixel point that enables the phasor value to reach the local minimum value as the initial seed point includes:

A phasor-error spectrum of each pixel point in the image in the predetermined resolution is obtained, and the phasor value that enables the pixel point to reach the local minimum value is determined according to the phasor-error spectrum; and if the pixel point has a signal-to-noise ratio greater than the predetermined value and has the unique phasor value, the pixel point is determined as the initial seed point.

A process of determining the pixel point having the unique phasor value may include:

if only one local minimum value of the pixel point enables the fitting error to be less than a predetermined value, the local minimum value is determined as the unique phasor value of the pixel point.

Step 13, the phasor value of a to-be-estimated pixel point is estimated according to the initial seed point to obtain a field pattern at a predetermined resolution.

A process of estimating the phasor value of the to-be-estimated pixel point includes:

if the to-be-estimated pixel point includes a plurality of local minimum values, then the local minimum values with the fitting errors less than the predetermined value is determined as a plurality of phasor values of the to-be-estimated pixel point; and the phasor value having the maximum similarity with the phasor value of adjacent seed points is selected from the plurality of phasor values of the to-be-estimated pixel point as the phasor value of the to-be-estimated pixel point.

Optionally, the phasor value of the to-be-estimated pixel point may be determined through the safest path-local growth algorithm, where the process thereof includes:

the to-be-estimated pixel point with an amplitude greater than a first threshold is selected to establish a first to-be-estimated pixel point set;

a phase difference between each two of adjacent seed points of each to-be-estimated pixel point in the first to-be-estimated pixel point set is obtained, and the to-be-estimated pixel point having a maximum phase difference less than a second threshold is selected to establish a second to-be-estimated pixel point set;

the to-be-estimated pixel points in the second to-be-estimated pixel point set are arranged in a descending order according to the number of the adjacent seed points, and a predetermined quantity of to-be-estimated pixel points are selected to establish a third to-be-estimated pixel point set;

the maximum phase similarity between the to-be-estimated pixel point in the third to-be-estimated pixel point set and the adjacent seed points is obtained, and the phasor value of the to-be-estimated pixel point having the similarity greater than a third threshold is taken as the phasor value of the to-be-estimated pixel point; and the to-be-estimated pixel point having the similarity greater than the third threshold is added to the to-be-estimated pixel point in the first to-be-estimated pixel point set for estimation, until the quantity of the adjacent seed points of the to-be-estimated pixel point in the first to-be-estimated pixel point set is zero.

Optionally, this step can also determine the phasor value of the to-be-estimated pixel point in the first to-be-estimated pixel point set, where the process thereof includes:

a fourth to-be-estimated pixel point set is determined by decreasing the first threshold by the predetermined quantity, and the factor phase value of the to-be-estimated pixel point in the fourth to-be-estimated pixel point set is determined until the first threshold is reduced to zero; and the phasor value of the to-be-estimated pixel point without the determined phasor value in the first to-be-estimated pixel point set is determined as an average value of the phasor values of the adjacent seed points.

Step 14, the field patterns at the predetermined resolutions are respectively mapped at the highest resolution to obtain a plurality of field patterns at the highest resolution; and a reconstructed field pattern is obtained after the plurality of field patterns are merged.

The mapping may refer to selecting the field pattern at the highest resolution by taking the field pattern at the predetermined resolution obtained in Step 13 as an initial value, where the process thereof includes:

the phase similarity between all phasor values of each reconstructed to-be-estimated pixel point at the highest resolution and the phasor value of the corresponding pixel point at the predetermined resolution is obtained, and the phasor value having the highest similarity is determined as the phasor value of the reconstructed to-be-estimated pixel point.

Step 15, the reconstructed seed point is determined from the reconstructed field pattern, and the estimation is conducted based on the reconstructed seed point to obtain the phasor value of the reconstructed to-be-estimated pixel point.

A process of determining the phasor value of the reconstructed to-be-estimated pixel point may include:

if the reconstructed to-be-estimated pixel point has the same phasor value in all field patterns, the reconstructed to-be-estimated pixel point is determined as a new seed point and the same phasor value is determined as the phasor value of the reconstructed to-be-estimated pixel point;

if the reconstructed to-be-estimated pixel point has different phasor values in all field patterns, the reconstructed to-be-estimated pixel point is reset as the to-be-estimated pixel point and the different phasor values are determined as the phasor candidate values; and by taking the new seed point as a starting point, the phasor candidate value may be estimated with the estimation method in Step 13 at the highest resolution to determine the phasor value of the reconstructed to-be-estimated pixel point.

Step 16, separated images of two predetermined components are obtained according to the phasor values of the reconstructed seed point and the reconstructed to-be-estimated pixel point.

After the phasor values of the reconstructed seed point and the reconstructed to-be-estimated pixel point are determined, the separated images of the two predetermined components may be obtained after smoothing with the reconstructed field pattern.

With the magnetic resonance chemical-shift-encoded imaging method proposed by the present embodiment, a region simultaneously including the two components may be identified as the seed point at the low resolution by estimating the field pattern at the low resolution, thereby increasing the quantity and distribution range of the seed points; and the plurality of field patterns having the high resolution are merged with a self-checking mechanism, thereby eliminating a deviation caused by the jump of the phasor value at the highest resolution, guaranteeing the correctness of final selection of the seed point and accurately identifying the signals of the two components.

A detailed description is made to the magnetic resonance chemical-shift-encoded imaging method below through specific embodiments:

Embodiment 1

A two-point MR (Magnetic Resonance) signal model including two components (taking water and fat as examples in the present embodiment) is:

$$S_n = (\rho_w + \rho_f e^{-i2\pi f_F TE_n}) e^{-i2\pi f_B TE_n}, n=1,2$$

$S_n$ indicates a signal strength at an echo time $TE_n$; n=1, 2 indicates the MR signal acquired at the two echo times in the present embodiment; $\rho_w$ and $\rho_f$ indicate the strength values of water and fat respectively; the chemical shift of the water is set as 0; $f_F$ indicates the chemical shift of the fat relative to the water, and can be set as −3.5 ppm in the present embodiment; and $f_B$ indicates a local field of a static magnetic field $B_o$. The parameters $c_1$, $c_2$, $d_0$ and d are defined as follows:

$$c_1 = e^{-i2\pi f_F TE_1}$$

$$c_2 = e^{-i2\pi f_B TE_2}$$

$$d_0 = e^{-2\pi f_F TE_1}$$

$$d = e^{-2\pi f_B \Delta TE}$$

where $\Delta TE = TE_1 - TE_2$, $d_0$ indicates the phase of the water caused by $f_B$ for the $TE_1$ time, and d indicates the phase accumulation caused by $f_B$ for the $\Delta TE$ time. In the present embodiment, d is called as the phasor (phasor), and the angle of the phasor is in a positive proportion to $f_B$, with the range of $[-\pi\ \pi]$. It can be known from the above formula that, d is a periodic function about $f_B$, and different $f_B$ having the same d may obtain the same result in a reconstructing process of the water and fat images. Therefore, in the present embodiment, the local field $f_B$ of the actual $B_o$ is not estimated, but only the phasor d is estimated, which also represents the nonuniformity of the local field of $B_o$, and may also be called as the field pattern.

If d is known, $d_0$ may be obtained from the above formula:

$$d_0 = \exp\left(i\angle \frac{S_1(1-c_2) - S_2(1-c_1)/d}{c_1 - c_2}\right)$$

The above MR signal model may be written as a matrix form:

$$S = A \begin{bmatrix} W \\ F \end{bmatrix}$$

wherein $S=[Re(\hat{S}_1);Re(\hat{S}_2);Im(\hat{S}_1);Im(\hat{S}_2)], \hat{S}_1=S_1/d_0, \hat{S}_2=S_2/(d_0 d)$, $$A = \begin{bmatrix} 1 & Re(c_1) \\ 1 & Re(c_2) \\ 0 & Im(c_1) \\ 0 & Im(c_2) \end{bmatrix};$$

Re indicates to take a plural real part, and Im indicates to take a plural imaginary part.

According to a variable projection (VARPRO), d may be obtained with the least square method:

$$d = \arg\min err(d) = \arg\min \|(1-AA^+)S\|^2$$

The above formula may be rewritten into the following form, and denoted as Formula 1:

$$d = \arg\min err(d) = \arg\min \Sigma(1-AA^+) \circ (SS^T)$$

wherein, I indicates 4×4 matrix; superscript '+' indicates to take matrix pseudo-inverse, and $A^+ = (A^T A)^{-1} A^T$; a connector "∘" indicates a dot product; err(d) describes a relationship between phasor d and the fitting error, and is expressed as the phasor-error spectrum which is defined as a corresponding model fitting error at the different phasor values; then the corresponding local minimum value is the corresponding phasor value of the pixel point. Most of pixels have two phasor values.

All pixel points in a volume of interest (VOI) are taken as a whole phasor-error spectrum, so that the following formula may be determined, and denoted as Formula 2:

$$S=[Re(\hat{S}_1);Re(\hat{S}_2);Im(\hat{S}_1);Im(\hat{S}_2)]$$

Wherein, $\hat{s}_1$ and $\hat{s}_1$ indicate row vectors, and each element represents a pixel point.

Figure 2:
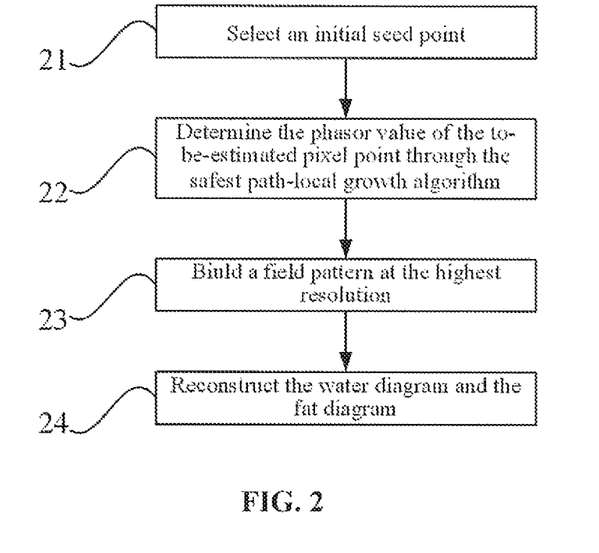
FIG. 2 is a flow chart illustrating an estimation method of a self-checking field pattern of safest path-local growth based on multiple resolutions in an example manner.

To select a correct phasor value from the plurality of pixel points, the present embodiment proposes a self-checking field pattern estimation method for a safest path-local growth based on multiple resolutions, thereby achieving correct selection of the phasor value. In combination with FIG. 2, the method includes:

Step 21, an initial seed point is selected.

In the present embodiment, the two-dimensional original image at the highest resolution is subjected to low-pass filtering and is undersampled according to the predefined undersampling coefficient to obtain the two-dimensional original images at different low resolutions. For example, the undersampling coefficient may be determined as [3 3], [5 5], [8 8] and [10 10], and then the original images at four groups of low resolutions may be obtained. Each pixel point in each image at the low resolution corresponds to a plurality of pixel points in the image at the highest resolution; the phasor-error spectrum of each pixel point at the low resolution may be obtained by taking the plurality of pixel points as a whole and describing the phasor-error spectrum according to the above Formula 1 and Formula 2; the phasor value that enables the pixel point to reach the local minimum value is found according to the phasor-error spectrum; and if the pixel point meets the following two conditions, the pixel point is marked as the seed point:

① the pixel point has a signal-to-noise ratio greater than a predetermined value: m>th, wherein m indicates the amplitude of the pixel point, and th indicates the threshold of the signal-to-noise ratio; and ② the pixel point has a unique phasor value: by taking A max and A min as the maximum and minimum of the phasor-error spectrum and taking a as the multiple of the fitting error, the threshold may be set as A min+α*(A max−A min). If only one local minimum value enables the fitting error to be less than the threshold, it is considered that the corresponding pixel point has the unique phasor value; otherwise, other local solutions of the pixel point, which are less than the threshold, are kept, and then the pixel point has a plurality of phasor values.

The amplitude m of the pixel point may be obtained by multiple calculation methods, such as:

$m=\max\{abs(S_1),abs(S_2)\}$ or $m=abs(S_1)+abs(S_2)$,etc

For selection of th and a, on the one hand, seed points with low SNR and a plurality of minimum value solutions are eliminated, and on the other hand, sufficient seed points should to be obtained. One candidate value may be: th is 0.2 time of the 98th percentile value of the amplitude of all pixels, and a is 0.4.

Figure 3:
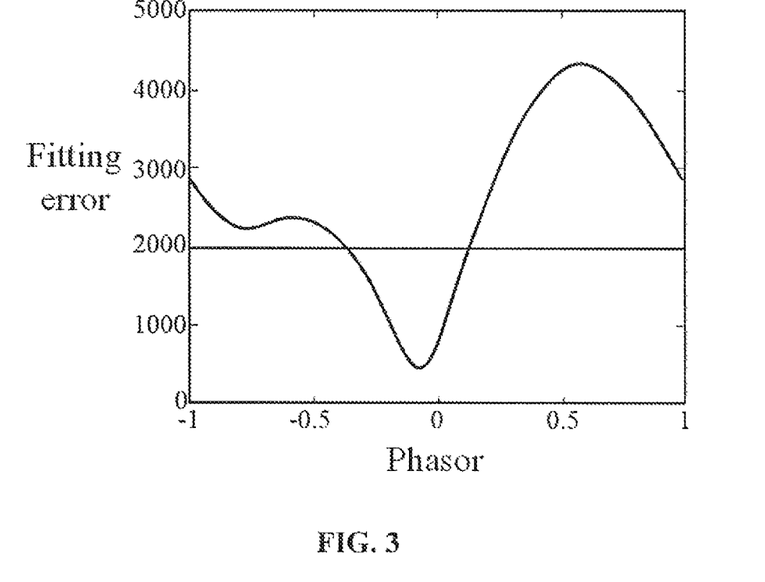
FIG. 3 illustrates a phasor-error spectrogram of a seed point in an example manner, wherein a horizontal coordinate indicates a phasor (that is, phase factor), a vertical coordinate indicates a corresponding fitting error (err(d), which is dimensionless), and a straight line in the figure indicates a threshold and a curve indicates a fitting error.

FIG. 3 shows the phasor-error spectrum of one seed point. The seed point only has one phasor value. For other pixel points with more than one phasor value (called as the to-be-estimated pixel point in the present embodiment, and the plurality of phasor values are collectively known as the phasor candidate value), a correct solution shall be selected from the following steps.

Optionally, the seed point is selected for the above four groups of images at the low resolution in this step. It should be noted that, the above four groups of images at the low resolution are only an example, and if other low resolutions are applicable to the present disclosure, other low resolutions should also be included in a protection scope of the present disclosure, which can be incorporated herein by reference.

Step 22, the phasor value of the to-be-estimated pixel point is determined through the safest path-local growth algorithm.

Based on the initial seed point, the following local growth algorithm is adopted by the present embodiment to complete the phasor estimation of the to-be-estimated pixel point, with the process including: a candidate value having the maximum similarity with the phasor value of the adjacent seed points is selected, from the phasor candidate values of the to-be-estimated pixel points, as the phasor value of the current to-be-estimated pixel point, i.e.:

$$d = \arg\max\{D_1, D_2, \ldots, D_S\},$$

wherein $D_s$ indicates the similarity of phasor, and defined as:

$$D_s = \frac{\sum_{k=1}^{K} m_k \cos(\text{angle}(d_s * \text{conj}(d_k)))}{\sum_{k=1}^{K} m_k}$$

wherein K indicates the quantity of seed points in eight neighborhoods (if the current to-be-estimated pixel point and the adjacent neighborhoods are divided into a sudoku format, eight adjacent regions other than the region of the current to-be-estimated pixel point are the eight neighborhoods) of the current to-be-estimated pixel point; $m_k$ indicates the amplitude of the k-th seed point, the corresponding phasor value is $d_k$, and $d_s$ indicates one phasor candidate value of the current to-be-estimated pixel point; conj(.) indicates to take complex conjugate; and angle(.) indicates to take an angle.

Optionally, in combination with FIG. 4, the safest path-local growth algorithm proposed by the present embodiment is as follows:

Step 221, the amplitude of each to-be-estimated pixel point is obtained through calculation from a predetermined amplitude diagram M;

Step 222, an amplitude threshold is set as $th_m$, and a to-be-estimated pixel point with an amplitude greater than $th_m$ is found to build a set which is denoted as U;

Step 223, a phasor difference between each two of adjacent seed points in all to-be-estimated pixel points in the set U is calculated, and if a maximum phasor difference is less than the threshold $th_p$, the corresponding to-be-estimated pixel point is kept, the kept to-be-estimated pixel point is built into a set which is denoted as V; and if a maximum phasor difference is greater than the threshold $th_p$, the corresponding to-be-estimated pixel point is removed;

Step 224, all the to-be-estimated pixel points in the set V are arranged in a descending order according to the quantity K of the adjacent seed points thereof;

Step 225, the first Q to-be-estimated pixel points arranged in the descending order are selected to establish a set denoted by L;

Step 226, a maximum phasor similarities between all the to-be-estimated pixel points in the set L and the adjacent seed points thereof are respectively calculated;

Step 227, if the similarity is greater than the threshold $th_p$, the corresponding candidate phasor value is selected as the phasor value of the to-be-estimated pixel point, and the pixel point is added as the seed point; otherwise, the pixel point is kept as the to-be-estimated pixel point;

Step 228, Steps 223-227 are repeated, until K is equal to 0;

Step 229, the amplitude threshold $th_v$ is decreased;

Step 230, Steps 222-229 are repeated, until the amplitude threshold $th_m$ is equal to 0; and Step 231, for the untreated to-be-estimated pixel points in Step 223 and Step 227, the phasor values thereof is selected as an average value of the phasor values of the adjacent seed points.

The above the safest path-local growth algorithm is separately conducted at each low resolution.

The amplitude of each pixel point in the amplitude diagram M may be defined as $m = \max\{abs(S_1), abs(S_2)\}$ or $m = abs(S_1) + abs(S_2)$ and the like. The amplitude threshold $th_m$ may be selected through several selection methods, and for example, can be selected according to the percentile value of all pixel amplitudes. The values of the threshold $th_D$ and the threshold $th_p$ may be determined (such as 0.9 and $\pi/2$) according to the smoothness of the candidate field pattern. The adjacent seed points of the to-be-estimated pixel point may be defined as the seed points in the four neighborhoods or eight neighborhoods thereof; and Q value may be ¼ of the quantity of the to-be-estimated pixel points in the set V.

Step 23, the field pattern at the highest resolution is established.

The field pattern at the highest resolution is selected by taking the field pattern at the low resolution obtained with the safest path-local growth algorithm in Step 22 as the initial value, and this process is called as field pattern mapping in the present embodiment, where the implementation process thereof may include: the phasor similarity between all phasor candidate values of each pixel point at the highest resolution and the phasor value of the corresponding pixel point at the low resolution is calculated, and the candidate value having the highest similarity is taken as the phasor value of the current pixel point.

In the present embodiment, selection of the seed point and the estimation of the local growth algorithm are respectively conducted at several different low resolutions. Therefore, a plurality of field patterns at the highest resolution are also obtained in this step, and then the plurality of field patterns are merged using the self-checking mechanism to obtain a field pattern, where the implementation process thereof may include: if one pixel point has the same phasor value in all the field patters, the pixel point is selected as a new seed point; and if one pixel point has different values in all field patters, the pixel point is reset as the to-be-estimated pixel point, and the phasor value of the to-be-estimated pixel point is one of the phasor candidate values.

With the above safest path-local growth algorithm, the selection of the phasor value of the to-be-estimated pixel point at the highest resolution is done by taking the new seed point as a starting point so as to obtain a final field pattern.

A principle of the step is the same as that of the local growth algorithm at the low resolution, and thus is not repeated in the present embodiment.

Step 24, the water diagram and the fat diagram are reconstructed.

The final field pattern obtained in Step 23 is smoothed, and then the water diagram and the fat diagram may be obtained by calculating with the following formula:

$$\begin{bmatrix} W \\ F \end{bmatrix} = A * S$$

wherein W and F respectively indicate the water diagram and the fat diagram obtained by calculation.

Figure 7:
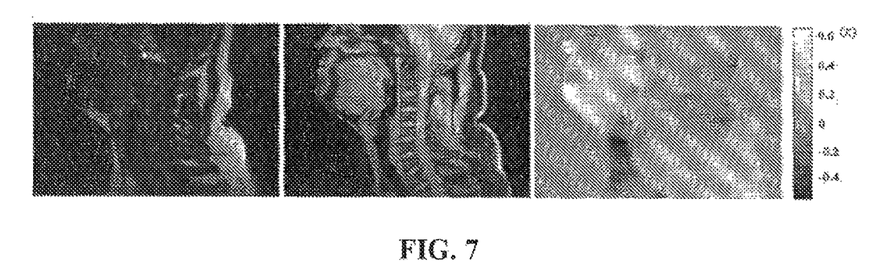
FIG. 7 is an instance diagram proposed by embodiment 1 to verify water-fat separation of a neck in the magnetic resonance chemical-shift-encoded imaging method, where an original image, a separated fat diagram, a separated water diagram and an estimated field pattern are located successively from left to right.
Figure 8:
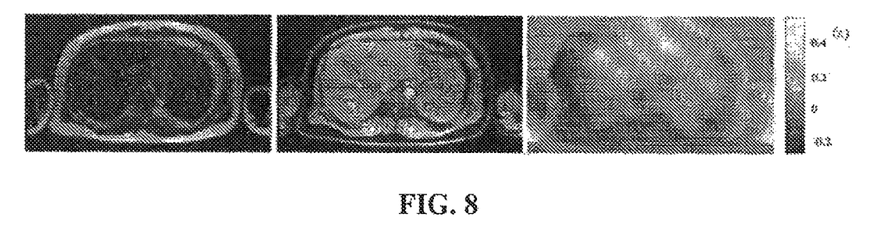
FIG. 8 is an instance diagram proposed by embodiment 1 to verify water-fat separation of an abdomen in the magnetic resonance chemical-shift-encoded imaging method, where an original image, a separated fat diagram, a separated water diagram and an estimated field pattern are located successively from left to right.

To verify feasibility of the magnetic resonance chemical-shift-encoded imaging method proposed by the present embodiment, tests are conducted in two body tissue experiments, and test objects are a neck and an abdomen. An acquisition sequence is FLASH; the main magnetic field is $B_o=3T$; and imaging parameters are (the neck/the abdomen): TR=200 ms/50 ms, a matrix size is 240×320/256×152, a layer thickness is 3/6 mm, a flip angle is 30°/25°, and TE=[4.64 5.51] ms. A processing environment of experimental data is a workstation having Intel E5-2650 v2 CPU and 64 GB RAM, and data processing software adopted is MATLAB. According to a final test result, it may be determined that, there is no tissue with obvious error separation in the water diagram and the fat diagram obtained in the body experiment. FIG. 7 and FIG. 8 show a separation result according to one layer of the neck and the abdomen. It may be seen that, there is no tissue with obvious error separation in the obtained water diagram and the fat diagram in the body tissue experiments.

It should be noted that, the magnetic resonance chemical-shift-encoded imaging method proposed by the present disclosure not only can be used for water-fat separation imaging, but also can be used for the application of separation of other chemical shift components, and a difference is only the corresponding chemical shift value inputted into the simplified MR signal model including the two components.

The magnetic resonance chemical-shift-encoded imaging method proposed by the present disclosure does not impose any limit to the TE, and may reach faster image acquisition speed, so that the method is applicable to some medical applications of rapid imaging, such as dynamic imaging and abdomen breathholding imaging. The proposed safest path-local growth algorithm may also have higher robustness in a region having a low signal-to-noise ratio compared with the existing local growth algorithm, Further, with the field pattern estimation and the local growth using multiple resolutions, the method proposed by the present embodiment can identify the region both including the water and the fat as the seed point at the low resolution, thereby increasing the quantity and the distribution range of the seed points. The field pattern estimation and the local growth at the low resolution are independent to each other, that is, processing between low resolutions has no any overlapping, which eliminates the influence of possible jump of the phasor value between different resolutions. The plurality of field patterns having the high resolution are merged with the self-checking mechanism, thereby eliminating the deviation caused by the jump of the phasor value at the highest resolution and guaranteeing the correctness of final selection of the seed points.

Figure 5:
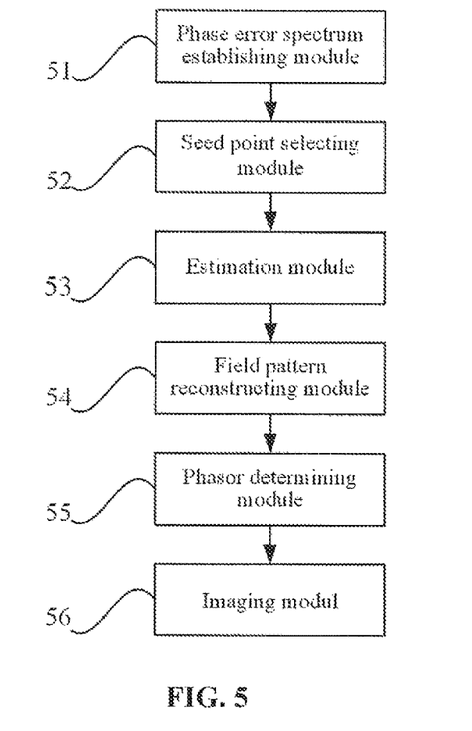
FIG. 5 is a structural drawing illustrating a magnetic resonance chemical-shift-encoded imaging apparatus in an example manner.

The present disclosure further proposes a magnetic resonance chemical-shift-encoded imaging apparatus. In combination with FIG. 5, the apparatus includes:

a phase error spectrum establishing module 51 configured to establish a phasor-error spectrum based on a two-point magnetic resonance signal model in a sampled image at a predetermined resolution;

a seed point selecting module 52 configured to determine, a pixel point having a unique phasor value in the phasor-error spectrum and enabling such spectrum to reach a local minimum value, as an initial seed point;

an estimation module 53 configured to estimate a phasor value of a to-be-estimated pixel point according to the initial seed point to obtain a field pattern at the predetermined resolution;

a field pattern reconstructing module 54 configured to map, at the highest resolution, the field patterns at the predetermined resolutions respectively to obtain a plurality of field patterns at the highest resolution, and merge the plurality of field patterns to obtain a reconstructed field pattern;

a phasor determining module 55 configured to determine a reconstructed seed point from the reconstructed field pattern and estimate the reconstructed seed point to obtain a phasor value of the reconstructed to-be-estimated pixel point; and an imaging module 56 configured to obtain separated images of two predetermined components according to the phasor values of the reconstructed to-be-estimated pixel point and the reconstructed seed point.

Optionally, the seed point selecting module 52 includes:

a local minimum value determining submodule configured to obtain the phasor-error spectrum of each pixel point in the image in the predetermined resolution and determine, according to the phasor-error spectrum, the phasor value that enables the pixel point to reach the local minimum value; and a seed point determining submodule configured to determine the pixel point as the initial seed point if the pixel point has a signal-to-noise ratio greater than the predetermined value and has the unique phasor value.

The seed point determining submodule may be configured to determine, if the to-be-estimated pixel point includes a plurality of local minimum values, the local minimum values with fitting errors less than the predetermined value as a plurality of phasor values of the to-be-estimated pixel point, and to select, from the plurality of phasor values of the to-be-estimated pixel point the phasor value having the maximum similarity with the phasor value of adjacent seed points, as the phasor value of the to-be-estimated pixel point.

Optionally, the estimation module 53 includes:

a first set establishing submodule configured to select the to-be-estimated pixel point having an amplitude greater than a first threshold to establish a first to-be-estimated pixel point set;

a second set establishing submodule configured to obtain a phase difference between each two of adjacent seed points of each to-be-estimated pixel point in the first to-be-estimated pixel point set, and select the to-be-estimated pixel point having a maximum phase difference less than a second threshold to establish a second to-be-estimated pixel point set;

a third set establishing submodule configured to arrange the to-be-estimated pixel points in the second to-be-estimated pixel point set according to the quantity of the adjacent seed points in a descending order, and select a predetermined quantity of to-be-estimated pixel points to establish a third to-be-estimated pixel point set;

a first phasor determining submodule configured to obtain a maximum phase similarity between the to-be-estimated pixel point in the third to-be-estimated pixel point set and the adjacent seed points, and take, the phasor value of the to-be-estimated pixel point having the similarity greater than a third threshold, as the phasor value of the to-be-estimated pixel point;

a first estimation submodule configured to estimate the to-be-estimated pixel point in the first to-be-estimated pixel point set by taking the to-be-estimated pixel point having the similarity greater than the third threshold as a new seed point, until the quantity of the adjacent seed points of the to-be-estimated pixel point in the first to-be-estimated pixel point set is zero;

a fourth set establishing module configured to decrease the first threshold by a predetermined quantity to determine a fourth to-be-estimated pixel point set;

a second phasor determining submodule configured to determine the phasor value of the to-be-estimated pixel point in the fourth to-be-estimated pixel point set, until the first threshold is decreased to zero; and a third phasor determining submodule configured to determine, the phasor value of the to-be-estimated pixel point without the determined phasor value in the first to-be-estimated pixel point set, as an average value of the phasor values of the adjacent seed points.

Optionally, the field pattern reconstructing module 54 includes:

a fourth phasor determining submodule configured to obtain the phase similarity between all phasor values of each reconstructed to-be-estimated pixel point at the highest resolution and the phasor value of the corresponding to-be-estimated pixel point at the predetermined resolution, and determine, the phasor value having the highest similarity, as the phasor value of the reconstructed to-be-estimated pixel point.

Optionally, the phasor determining module 55 includes:

a fifth phasor determining submodule configured to determine the reconstructed to-be-estimated pixel point as the new seed point and determine the same phasor value as the phasor value of the reconstructed to-be-estimated pixel point, if the reconstructed to-be-estimated pixel point has the same phasor value in all field patterns;

a sixth phasor determining submodule configured to reset the reconstructed to-be-estimated pixel point as the to-be-estimated pixel point and determine different phasor values as phasor candidate values, if the reconstructed to-be-estimated pixel point has different phasor values in all field patterns; and a seventh phasor determining submodule configured to estimate the phasor candidate value at the highest resolution by taking the new seed point as a starting point to determine the phasor value of the reconstructed to-be-estimated pixel point.

With the magnetic resonance chemical-shift-encoded imaging apparatus proposed by the present embodiment, a region including the two components may be identified as the seed point at the low resolution by estimating the field pattern at the low resolution, thereby increasing the quantity and distribution range of the seed points; and the plurality of field patterns having the high resolution are merged with a self-checking mechanism, thereby eliminating the deviation caused by the jump of the phasor value at the highest resolution, guaranteeing the correctness of final selection of the seed points and accurately identifying the signals of the two components.

The present disclosure further proposes a device including a processor and a memory configured to store computer readable instructions. The processor is configured to execute the method as stated in embodiment 1 by executing the computer readable instructions.

Figure 4:
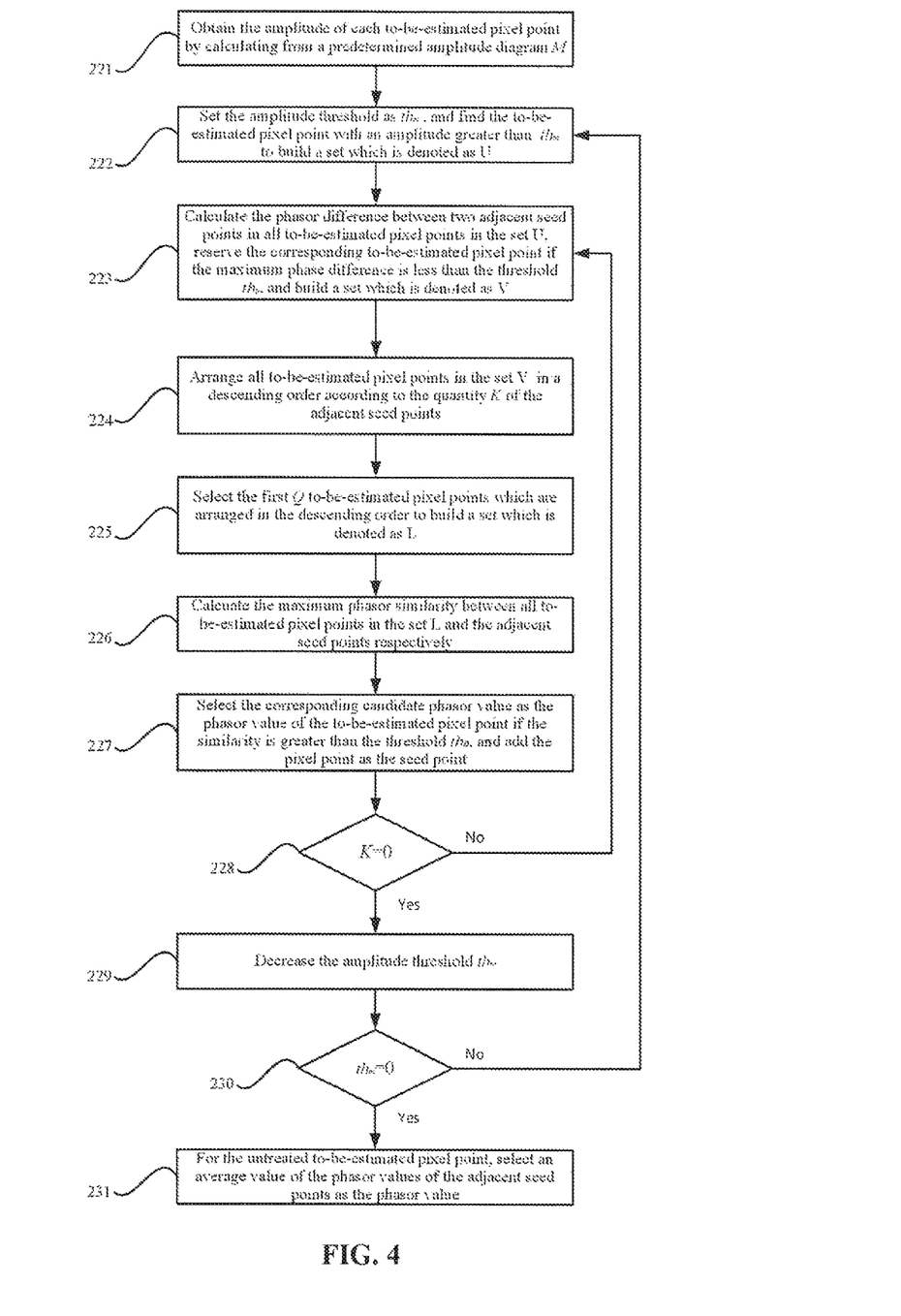
FIG. 4 is a flow chart illustrating a safest path-local growth algorithm in an example manner.
Figure 6:
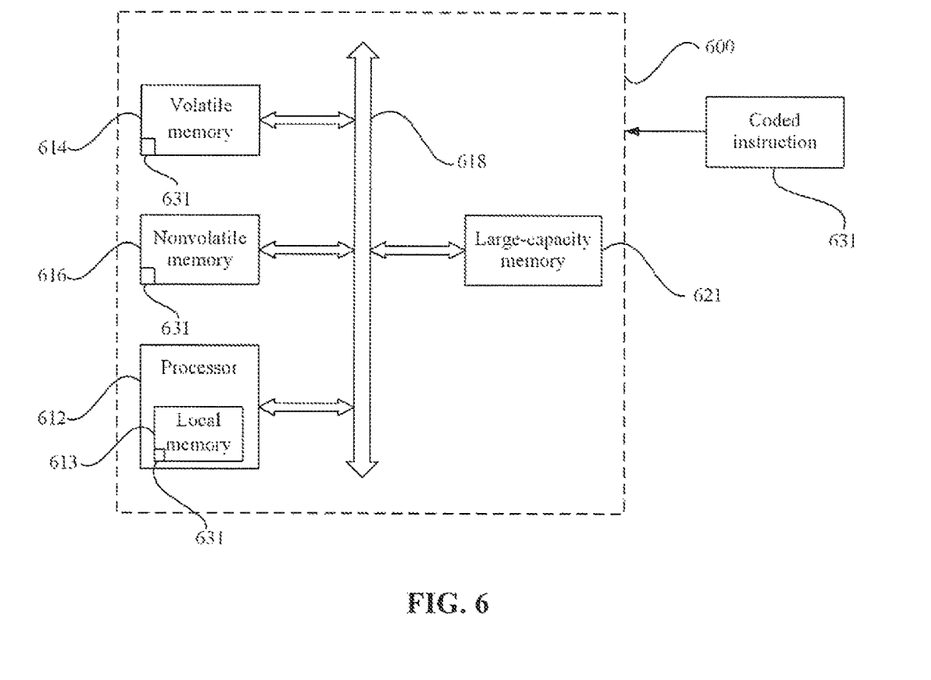
FIG. 6 is a structural drawing illustrating a computer device in an example manner.

FIG. 6 is a block diagram of an exemplary processor platform 600 capable of executing an instruction flow shown in FIG. 4 and having an exemplary magnetic resonance chemical-shift-encoded imaging in FIG. 5. The processor platform 600 may be a server, a personal computer or any other kinds of computer equipment.

The processor platform 600 shown in FIG. 6 includes a processor 612. For example, the processor 612 may be realized by one or more microprocessors or controllers from any expected family or manufacturer.

The processor 612 includes a local memory 613 (for example, a cache memory), and is communicated with a main memory through a bus 618. The main memory includes a volatile memory 614 and a nonvolatile memory 616. The volatile memory 614 may be realized by a synchronous dynamic random access memory (SDRAM), a dynamic random access memory (DRAM), RAM bus (RAMBUS) dynamic random access memory (DRAM) and/or any other kinds of random access memory devices. The nonvolatile memory 616 may be realized by a flash memory and/or any other expected kinds of storage devices. Access to the volatile memory 614 and the nonvolatile memory 616 is controlled by a memory controller.

The processor platform 600 may also include one or more large-capacity storage apparatuses 621 for storing software and data. Examples of such the large-capacity storage apparatuses 621 include a floppy disk drive, a hard disk drive, an optical disk drive and a digital versatile disc (DVD) drive. A coded instruction 631 shown in FIG. 6 may be stored in the large-capacity storage apparatus 621, the volatile memory 614, the nonvolatile memory 616 and/or a mobile storage medium, such as CD or DVD.

Specific embodiments describe the technical solution of the present disclosure clearly and completely, and embodiments therein are only some embodiments of the present disclosure, rather than all embodiments. Based on embodiments in the present disclosure, all of other embodiments obtained by those skilled in the art without creative labor belong to the protection scope of the present disclosure.

What is claimed is:

1. A magnetic resonance chemical-shift-encoded imaging method, comprising:
   providing predetermined resolutions;
   establishing a phasor-error spectrum based on a two-point magnetic resonance signal model in a sampled image at each of the predetermined resolutions;
   determining to be an initial seed point a pixel point having a unique phasor value in the phasor-error spectrum and enabling the phasor-error spectrum to reach a local minimum value;
   estimating a phasor value of a to-be-estimated pixel point according to the initial seed point to obtain a field pattern at each of the predetermined resolutions;
   mapping, at a highest resolution, the field patterns at the predetermined resolutions respectively to obtain a plurality of field patterns at the highest resolution, and merging the plurality of field patterns to obtain a reconstructed field pattern;

determining a reconstructed seed point from the reconstructed field pattern, and estimating based on the reconstructed seed point to obtain a phasor value of the reconstructed to-be-estimated pixel point; and obtaining separated images of two predetermined components according to the phasor values of the reconstructed to-be-estimated pixel point and the reconstructed seed point.

2. The method according to claim 1, wherein obtaining separated images of two predetermined components according to the phasor values of the reconstructed to-be-estimated pixel point and the reconstructed seed point comprises:

obtaining the separated images of the two predetermined components after smoothing the reconstructed field pattern.

3. A computer readable storage medium, comprising computer instructions, when the computer instructions are executed, executing the method of claim 1.

4. The method according to claim 1, wherein determining to be the initial seed point the pixel point having a unique phasor value and enabling the phasor-error spectrum to reach the local minimum value comprises:

obtaining a phasor-error spectrum of each pixel point in the image in the predetermined resolution, and determining, according to the phasor-error spectrum, the phasor value that enables the pixel point to reach the local minimum value; and determining the pixel point to be the initial seed point if the pixel point has a signal-to-noise ratio greater than the predetermined value and has a unique phasor value.

5. The method according to claim 4, wherein determining the pixel point having the unique phasor value comprises:

determining, if the pixel point has only one local minimum value enabling the fitting error to be less than a predetermined value, the local minimum value to be the unique phasor value of the pixel point.

6. The method according to claim 4, wherein the phasor-error spectrum is determined through the following formula:

$$d = \arg\min \operatorname{err}(d) = \arg\min \Sigma (1 - AA^+) \circ (SS^T)$$

$$S = [\operatorname{Re}(\hat{s}_1); \operatorname{Re}(\hat{s}_2); \operatorname{Im}(\hat{s}_1); \operatorname{Im}(\hat{s}_2)],$$

wherein d indicates the phasor-error spectrum; I indicates 4×4 matrix; superscript '+' indicates to take matrix pseudo-inverse, $A^+ = (A^T A)^{-1} A^T$; a connector "$\circ$" indicates a dot product; err(d) describes a relationship between phasor d and the fitting error; and $\hat{s}_1$ and $\hat{s}_2$ indicate predetermined row vectors.

7. The method according to claim 5, wherein estimating the phasor value of the to-be-estimated pixel point according to the initial seed point comprises:

determining, if the to-be-estimated pixel point comprises a plurality of local minimum values, the local minimum values having the fitting errors less than the predetermined value to be a plurality of phasor values of the to-be-estimated pixel point; and selecting, from the plurality of phasor values of the to-be-estimated pixel point, the phasor value having the maximum similarity with the phasor values of adjacent seed points to be the phasor value of the to-be-estimated pixel point.

8. The method according to claim 7, wherein a maximum similarity between a plurality of phasor values of the to-be-estimated pixel point and phasor values of adjacent seed points is determined through the following formula:

$$d = \arg\max\{D_1, D_2, \ldots, D_S\}$$

wherein $D_1, D_2 \ldots D_s$ indicate the similarity of phasor and are determined through the following formula:

$$D_s = \frac{\sum_{k=1}^{K} m_k \cos(\operatorname{angle}(d_s * \operatorname{conj}(d_k)))}{\sum_{k=1}^{K} m_k}$$

wherein K indicates the quantity of seed points in eight neighborhoods of the current to-be-estimated pixel point; $m_k$ indicates the amplitude of the k-th seed point; the corresponding phasor value is $d_k$, which indicates a phasor candidate value of the current to-be-estimated pixel point; conj(.) indicates to take complex conjugate; and angle(.) indicates to take an angle.

9. The method according to claim 8, wherein estimating the phasor value of the to-be-estimated pixel point according to the initial seed point further comprises:

selecting the to-be-estimated pixel point having an amplitude greater than a first threshold to establish a first to-be-estimated pixel point set;

obtaining a phase difference between each two of adjacent seed points of each to-be-estimated pixel point in the first to-be-estimated pixel point set, and selecting the to-be-estimated pixel point having a maximum phase difference less than a second threshold to establish a second to-be-estimated pixel point set;

arranging to-be-estimated pixel points in the second to-be-estimated pixel point set in a descending order based on the quantity of the adjacent seed points, and selecting a predetermined quantity of to-be-estimated pixel points to establish a third to-be-estimated pixel point set;

obtaining the maximum phase similarity between the to-be-estimated pixel points in the third to-be-estimated pixel point set and the adjacent seed points, and taking the phasor value of the to-be-estimated pixel point having the similarity greater than a third threshold to be the phasor value of the to-be-estimated pixel point; and adding the to-be-estimated pixel point having the similarity greater than the third threshold to be the seed point to estimate the to-be-estimated pixel point in the first to-be-estimated pixel point set, until the quantity of the adjacent seed points of the to-be-estimated pixel point in the first to-be-estimated pixel point set is zero.

10. The method according to claim 9, wherein estimating the phasor value of the to-be-estimated pixel point according to the initial seed point further comprises:

determining a fourth to-be-estimated pixel point set by decreasing the first threshold by the predetermined quantity, and determining the factor phase value of the to-be-estimated pixel point in the fourth to-be-estimated pixel point set, until the first threshold is reduced to zero; and determining the phasor value of the to-be-estimated pixel point without the determined phasor value in the first to-be-estimated pixel point set to be an average value of the phasor values of the adjacent seed points.

11. The method according to claim 1, wherein mapping at a highest resolution a plurality of field patterns at the predetermined resolutions respectively comprises:

obtaining the phase similarity between all phasor values of each reconstructed to-be-estimated pixel point at the highest resolution and the phasor value of the corresponding pixel point at the predetermined resolution, and determining the phasor value having the highest similarity as the phasor value of the reconstructed to-be-estimated pixel point.

12. The method according to claim 11, wherein determining the phasor value of the reconstructed to-be-estimated pixel point comprises:
determining the reconstructed to-be-estimated pixel point to be a new seed point and determining the same phasor value to be the phasor value of the reconstructed to-be-estimated pixel point, if the reconstructed to-be-estimated pixel point has the same phasor value in all field patterns; and
resetting the reconstructed to-be-estimated pixel point to be the to-be-estimated pixel point and determining the different phasor values to be the phasor candidate values, if the reconstructed to-be-estimated pixel point has different phasor values in all field patterns.

13. The method according to claim 12, wherein determining the phasor value of the reconstructed to-be-estimated pixel point further comprises:
estimating the phasor candidate value at the highest resolution by taking the new seed point as a starting point, to determine the phasor value of the reconstructed to-be-estimated pixel point.

14. A magnetic resonance chemical-shift-encoded imaging apparatus, comprising:
a phase error spectrum establishing module, configured to establish a phasor-error spectrum based on a two-point magnetic resonance signal model in a sampled image at each of predetermined resolutions;
a seed point selecting module, configured to determine to be an initial seed point a pixel point having a unique phasor value in the phasor-error spectrum and enabling the phasor-error spectrum to reach a local minimum value;
an estimation module, configured to estimate a phasor value of a to-be-estimated pixel point according to the initial seed point to obtain a field pattern at each of the predetermined resolutions;
a field pattern reconstructing module configured to map, at a highest resolution, the field patterns at the predetermined resolutions respectively to obtain a plurality of field patterns at the highest resolution, and merge the plurality of field patterns to obtain a reconstructed field pattern;
a phasor determining module, configured to determine a reconstructed seed point in the reconstructed field pattern, and estimate based on the reconstructed seed point to obtain a phasor value of the reconstructed to-be-estimated pixel point; and
an imaging module, configured to obtain separated images of two predetermined components according to the phasor values of the reconstructed to-be-estimated pixel point and the reconstructed seed point.

15. The apparatus according to claim 14, wherein the seed point selecting module comprises:
a local minimum value determining submodule, configured to obtain the phasor-error spectrum of each pixel point in the image in the predetermined resolution and determine, according to the phasor-error spectrum, the phasor value that enables the pixel point to reach the local minimum value; and
a seed point determining submodule, configured to determine the pixel point to be the initial seed point if the pixel point has a signal-to-noise ratio greater than the predetermined value and has a unique phasor value.

16. The apparatus according to claim 15, wherein the seed point determining submodule is configured to determine, if the to-be-estimated pixel point comprises a plurality of local minimum values, the local minimum values having fitting errors less than the predetermined value to be a plurality of phasor values of the to-be-estimated pixel point, and to select, from the plurality of phasor values of the to-be-estimated pixel point, the phasor value having the maximum similarity with the phasor values of adjacent seed points to be the phasor value of the to-be-estimated pixel point.

17. The apparatus according to claim 16, wherein the estimation module comprises:
a first set establishing submodule, configured to select the to-be-estimated pixel point having an amplitude greater than a first threshold to establish a first to-be-estimated pixel point set;
a second set establishing submodule, configured to obtain a phase difference between each two of adjacent seed points of each to-be-estimated pixel point in the first to-be-estimated pixel point set, and select the to-be-estimated pixel point having a maximum phase difference less than a second threshold to establish a second to-be-estimated pixel point set;
a third set establishing submodule, configured to arrange the to-be-estimated pixel points in the second to-be-estimated pixel point set according to the quantity of the adjacent seed points in a descending order, and select a predetermined quantity of to-be-estimated pixel points to establish a third to-be-estimated pixel point set;
a first phasor determining submodule, configured to obtain a maximum phase similarity between the to-be-estimated pixel point in the third to-be-estimated pixel point set and the adjacent seed points, and take the phasor value of the to-be-estimated pixel point with the similarity greater than a third threshold to be the phasor value of the to-be-estimated pixel point; and
a first estimation submodule, configured to estimate the to-be-estimated pixel point in the first to-be-estimated pixel point set by taking the to-be-estimated pixel point having the similarity greater than the third threshold as a new seed point, until the quantity of the adjacent seed points of the to-be-estimated pixel point in the first to-be-estimated pixel point set is zero.

18. The apparatus according to claim 17, wherein the estimation module further comprises:
a fourth set establishing module, configured to decrease the first threshold by a predetermined quantity to determine a fourth to-be-estimated pixel point set;
a second phasor determining submodule, configured to determine the phasor value of the to-be-estimated pixel point in the fourth to-be-estimated pixel point set, until the first threshold is decreased to zero; and
a third phasor determining submodule, configured to determine, the phasor value of the to-be-estimated pixel point without the determined phasor value in the first to-be-estimated pixel point set, to be an average value of the phasor values of the adjacent seed points.

19. The apparatus according to claim 14, wherein the field pattern reconstructing module comprises:
a fourth phasor determining submodule, configured to obtain the phase similarity between all phasor values of each reconstructed to-be-estimated pixel point at the highest resolution and the phasor value of the corresponding to-be-estimated pixel point at the predetermined resolution, and determine, the phasor value having the highest similarity, to be the phasor value of the reconstructed to-be-estimated pixel point.

20. The apparatus according to claim 19, wherein the phasor determining module comprises:
a fifth phasor determining submodule, configured to determine the reconstructed to-be-estimated pixel point to be the new seed point and determine the same phasor value to be the phasor value of the reconstructed to-be-estimated pixel point, if the reconstructed to-be-estimated pixel point has the same phasor value in all field patterns;
a sixth phasor determining submodule configured to reset the reconstructed to-be-estimated pixel point to be the to-be-estimated pixel point and determine different phasor values to be phasor candidate values, if the reconstructed to-be-estimated pixel point has different phasor values in all field patterns; and
a seventh phasor determining submodule, configured to estimate the phasor candidate value at the highest resolution by taking the new seed point as a starting point to determine the phasor value of the reconstructed to-be-estimated pixel point.

* * * * *